(12) United States Patent
Park et al.

(10) Patent No.: US 7,575,899 B2
(45) Date of Patent: Aug. 18, 2009

(54) **MICROORGANISM OF THE GENUS *CORYNEBACTERIUM* HAVING ENHANCED L-LYSINE PRODUCTIVITY AND METHOD OF PRODUCING L-LYSINE USING THE MICROORGANISM OF THE GENUS *CORYNEBACTERIUM***

(75) Inventors: Young Hoon Park, Seongnam (KR); Hyun Min Koo, Goyang (KR); Sang Jo Lim, Icheon (KR); Jun Ok Moon, Seoul (KR); Young Lyeol Yang, Goyang (KR)

(73) Assignee: CJ Cheiljedang Corporation, Seoul (KR)

( * ) Notice: Subject to any disclaimer, the term of this patent is extended or adjusted under 35 U.S.C. 154(b) by 338 days.

(21) Appl. No.: 11/562,176

(22) Filed: Nov. 21, 2006

(65) Prior Publication Data

US 2007/0178564 A1    Aug. 2, 2007

(30) Foreign Application Priority Data

Nov. 30, 2005  (KR) .................... 10-2005-0115904

(51) Int. Cl.
*C12P 21/04* (2006.01)
(52) U.S. Cl. .................. 435/71.1; 435/243; 435/252.1; 536/23.1
(58) Field of Classification Search ............. 435/243, 435/252.1, 71.1; 536/23.1
See application file for complete search history.

(56) References Cited

U.S. PATENT DOCUMENTS

| 5,766,925 | A  | 6/1998 | Sugimoto et al. |
| 6,872,553 | B2 | 3/2005 | Eikmanns et al. |

FOREIGN PATENT DOCUMENTS

WO    01/00844 A2    1/2001

OTHER PUBLICATIONS

Nakagawa et al., "The *Corynebacterium glutamicum* genome: features and impacts on biotechnological processes." Appl Microbiol Biotechnol. Aug. 2003:62(2-3):99-109. Epub May 13, 2003 English abstract only, with related NCBI sequence transmission.
Last Non-Final Rejection issued by the Korean Intellectual Property Office for KR 10-2005-0115906 with English translation. 5 pages.
Ikeda et al., "The *Corynebacterium glutamicum* genome: features and impacts on biotechnological processes", Appl Microbio Biotechnol, 2003, vol. 62, pp. 99-109; XP002419971.
Kalinowski et al., "The complete *Corynebacterium glutamicum* ATCC 13032 genome sequence . . . ", Journal of Biotechnology, 2003, vol. 104, pp. 5-25; XP001184752.

*Primary Examiner*—Jennifer E Graser
(74) *Attorney, Agent, or Firm*—Rothwell, Figg, Ernst & Manbeck

(57) ABSTRACT

The present invention provides a microorganism that belongs to the genus *Corynebacterium* and has an inactivated inherent NCgl2053 dehydrogenase gene, and a method of producing L-lysine using the same. By using the microorganism, the yield of L-lysine is increased since an inherent NCgl2053 dehydrogenase gene is inactivated. According to the method, L-lysine can be produced with high yield.

8 Claims, 1 Drawing Sheet

SEQUENCE LISTING

<160> NUMBER OF SEQ ID NOS: 6

<210> SEQ ID NO 1
<211> LENGTH: 888
<212> TYPE: DNA
<213> ORGANISM: Corynebacterium glutamicum ATCC 13032
<220> FEATURE:
<221> NAME/KEY: gene
<222> LOCATION: (1)..(879)
<223> OTHER INFORMATION: NCgl2053 gene

<400> SEQUENCE: 1

| | | | | | |
|---|---|---|---|---|---|
| atgatttcat | tgctaaatga | tccacgtacg | ctattcccga | aagtcgatcc | cccaaagcaa | 60 |
| agccagccgg | aaccaggcct | agatataaaa | ctttccccccc | aagccgatat | tggtctctcc | 120 |
| agctatcaag | gaagtggaag | gcttaagggc | cgcaaggctc | ttattactgg | tggcgattct | 180 |
| gggattggag | ctgccgtagc | aatcgcttat | gctcgcgagg | gggcagatgt | tgcgatcgct | 240 |
| tacttgcccg | aagaacaagc | cgatgctgac | agagtgctcc | aagcaatcga | ggaaacaggt | 300 |
| caaaaagctt | tttctttccc | tggtgatctc | cgtgatccag | aatactgtcg | ctcgctggtc | 360 |
| caagagacgt | gaacgctttt | aggtggccta | gacatcttgg | tcaacaacgc | gtcacgtcag | 420 |
| gtgtgggcac | ctggtttgac | cgaaattacc | gacgaaaact | tcgaccagac | tttgcaggtt | 480 |
| aacctctatg | gtagttttcg | ggttaccaaa | gcagctatac | ctcatctgaa | gcccggatca | 540 |
| tcgataatct | ttacatcgtc | cattcaggcg | taccaacctt | cggaacccct | cttggattac | 600 |
| gccatgacta | aggcggcatt | gaacaatttg | tcaaagggct | tggcaagtag | tctgataggc | 660 |
| gatggcattc | gggtaaattc | tgtagcccca | ggtcctttct | ggacgccgtt | gcaacccagc | 720 |
| catggtcagc | cacaagagaa | aatagaagga | tttggccagc | acgctccgat | tggaagagcg | 780 |
| ggtcaccctg | ttgagttggc | aggtgcgtac | gtttttctcg | cttctgacga | agccagctat | 840 |
| gtggtaggag | aaaccctggg | agtcacaggt | gggacgccca | ccccatag | | 888 |

<210> SEQ ID NO 2
<211> LENGTH: 500
<212> TYPE: DNA
<213> ORGANISM: Artificial Sequence
<220> FEATURE:
<223> OTHER INFORMATION: A segment of Corynebacterim glutamicum ATCC
      13032 NCgl 2053 gene

<400> SEQUENCE: 2

| | | | | | |
|---|---|---|---|---|---|
| gtggcgattc | tgggattgga | gctgccgtag | caatcgctta | tgctcgcgag | ggggcagatg | 60 |
| ttgcgatcgc | ttacttgccc | gaagaacaag | ccgatgctga | cagagtgctc | caagcaatcg | 120 |
| aggaaacagg | tcaaaaagct | tttctttcc | ctggtgatct | ccgtgatcca | gaatactgtc | 180 |
| gctcgctggt | ccaagagacg | tgaacgctt | aggtggcct | agacatcttg | gtcaacaacg | 240 |
| cgtcacgtca | ggtgtgggca | cctggtttga | ccgaaattac | cgacgaaaac | ttcgaccaga | 300 |
| ctttgcaggt | taacctctat | ggtagttttc | gggttaccaa | agcagctata | cctcatctga | 360 |
| agcccggatc | atcgataatc | tttacatcgt | ccattcaggc | gtaccaacct | tcggaacccc | 420 |
| tcttggatta | cgccatgact | aaggcggcat | tgaacaattt | gtcaaagggc | ttggcaagta | 480 |
| gtctgatagg | cgatggcatt | | | | | 500 |

```
<210> SEQ ID NO 3
<211> LENGTH: 20
<212> TYPE: DNA
<213> ORGANISM: Artificial Sequence
<220> FEATURE:
<223> OTHER INFORMATION: primer 1 for amplifying a partial region
      (170-650nt) of NCgl2053 gene

<400> SEQUENCE: 3
gtggcgattc tgggattgga                                                 20

<210> SEQ ID NO 4
<211> LENGTH: 20
<212> TYPE: DNA
<213> ORGANISM: Artificial Sequence
<220> FEATURE:
<223> OTHER INFORMATION: primer 2 for amplifying a partial region
      (170-650nt) of NCgl2053 gene

<400> SEQUENCE: 4
aatgccatcg cctatcagac                                                 20

<210> SEQ ID NO 5
<211> LENGTH: 20
<212> TYPE: DNA
<213> ORGANISM: Artificial Sequence
<220> FEATURE:
<223> OTHER INFORMATION: primer 3 for amplifying a partial region
      (118-775nt) of NCgl2053 gene

<400> SEQUENCE: 5
tccagctatc aaggaagtgg                                                 20

<210> SEQ ID NO 6
<211> LENGTH: 20
<212> TYPE: DNA
<213> ORGANISM: Artificial Sequence
<220> FEATURE:
<223> OTHER INFORMATION: primer 4 for amplifying a partial region
      (118-775nt) of NCgl2053 gene

<400> SEQUENCE: 6
ttccaatcgg agcgtgctgg                                                 20
```

MICROORGANISM OF THE GENUS *CORYNEBACTERIUM* HAVING ENHANCED L-LYSINE PRODUCTIVITY AND METHOD OF PRODUCING L-LYSINE USING THE MICROORGANISM OF THE GENUS *CORYNEBACTERIUM*

CROSS-REFERENCE TO RELATED PATENT APPLICATION

This application claims the benefit of Korean Patent Application No. 10-2005-0115904, filed on Nov. 30, 2005, in the Korean Intellectual Property Office, the disclosure of which is incorporated herein in its entirety by reference.

BACKGROUND OF THE INVENTION

1. Field of the Invention

The present invention relates to a microorganism that belongs to the genus *Corynebacterium* and has enhanced L-lysine productivity and a method of producing L-lysine using the same.

2. Description of the Related Art

A strain of the genus *Corynebacterium*, particularly *Corynebacterium glutamicum*, is a microorganism which is extensively used to produce L-amino acid. L-amino acid, particularly L-lysine, is used to produce feed for animals and medicines for humans, and is also used in the pharmaceutics industry. L-amino acid is produced through the fermentation of the *Corynebacterium* strain, but since the method by which L-amino acid is produced using the genus *Corynebacterium* is important, there have been extensive attempts to improve the method.

One such attempt to improve L-amino acid production using a strain of the genus *Corynebacterium* involves destroying or attenuating the expression of a specific gene using recombinant DNA technology. For example, in U.S. Pat. No. 6,872,553, there is provided a process for the fermentative preparation of L-amino acids, the process including a) a growing stage of the *Corynebacterium* in which DNA encoding of phosphoenol pyruvate (PEP) carboxykinase (pck) is attenuated by a method of mutagenesis selected from the group consisting of insertion mutagenesis by insertion of at least one base pair, deletion mutagenesis with deletion of at least one base pair, and transition or transversion mutagenesis with incorporation of a non-sense mutation of the activity of said polypeptide is reduced as compared to an unattenuated *Corynebacterium*; b) a concentrating stage of the desired L-amino acid product in the medium or cells of said bacteria; and c) an isolating stage of separating said L-amino acid product.

Also, there has been extensive research into the effects of amplifying genes which relate to the biosynthesis of individual L-amino acid on the production of L-amino acid, and into the improvement of the L-amino acid producing *Corynebacterium* strain (Eggeling, Amino Acids 6, 261-272 (1994).) In addition, there have been attempts to introduce a foreign gene of different bacterial origin. For example, in Japanese Published Application No. Hei 7-121228, there is provided a process of culturing a microorganism which belongs to the genus *Corynebacterium* or the genus *Brevibacterium* and possesses a DNA fragment having gene information related to the synthesis of citric acid synthase of a microorganism and recombinant DNA of vector DNA, and a method of producing L-glutamic acids and L-proline in the medium.

However, according to said methods, the use of a strain having enhanced L-lysine productivity is desired.

SUMMARY OF THE INVENTION

The present invention provides a microorganism that belongs to the genus *Corynebacterium* and has enhanced L-lysine productivity.

The present invention also provides a method of producing L-lysine using the microorganism of the genus *Corynebacterium*.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
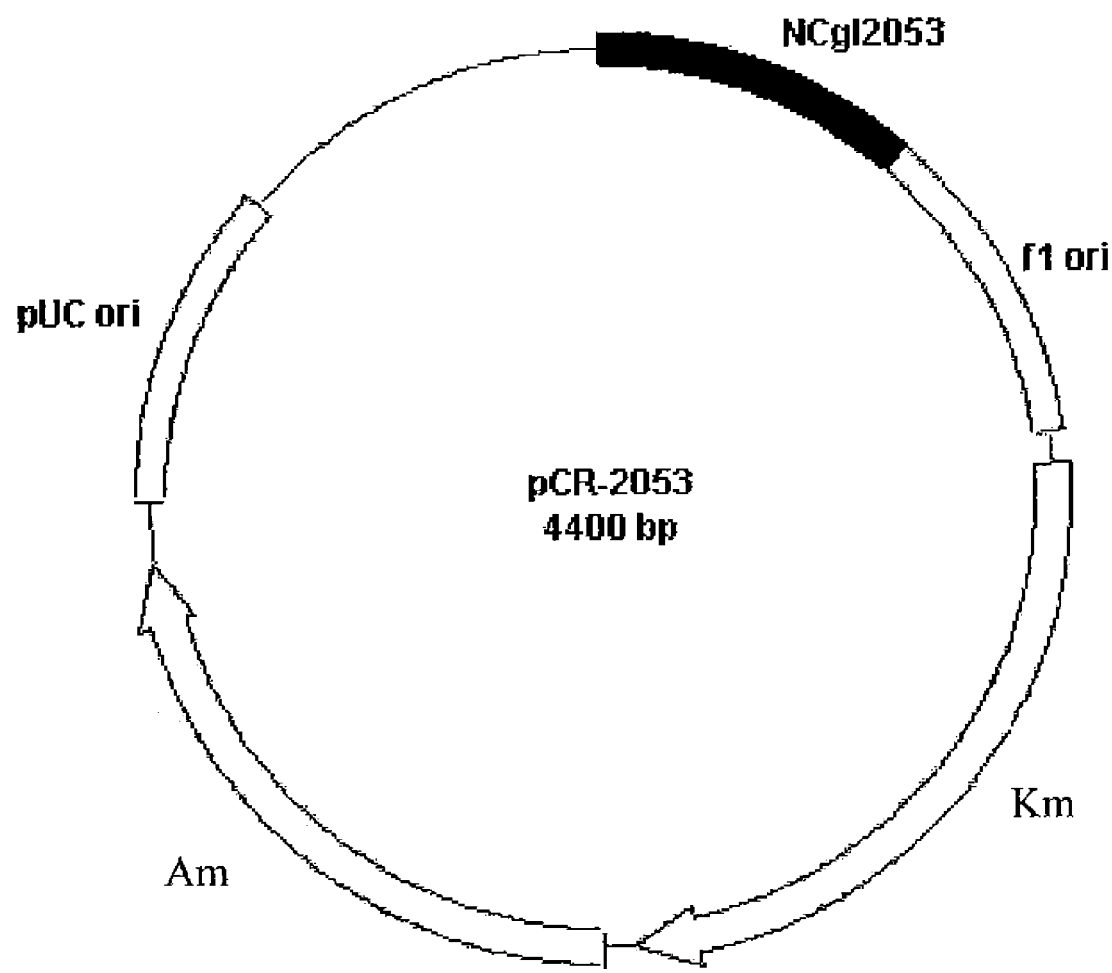
FIG. 1 is a diagram illustrating a pCR-2053 vector cloned with an NCgl2053 gene fragment of about 500 bp.

According to an aspect of the present invention, there is provided a microorganism that belongs to the genus *Corynebacterium* that has an inherent NCgl2053 dehydrogenase gene that is inactivated and produces lysine.

The inherent NCgl2053 dehydrogenase gene has dehydrogenase activity, and exists inherently in a microorganism of the genus *Corynebacterium* (Nakagawa, Appl. Microbiol. Biotechnol. 62(2-3), 99-109 (2003).). The activity of the dehydrogenase gene is estimated from a complete sequence analysis of the genome of *Corynebacterium glutamicum* ATCC 13032. The dehydrogenase gene can have the nucleotide sequence of SEQ ID No: 1.

A microorganism that belongs to the genus *Corynebacterium* and has an inactivated inherent NCgl2053 dehydrogenase gene according to an embodiment of the present invention may be *Corynebacterium glutamicum* ATCC 13032, *Corynebacterium thermoaminogenes* FERM BP-1539, *Corynebacterium glutamicum* KFCC 10881, or *Corynebacterium glutamicum* KFCC 11001, but is not limited to these examples.

The inactivation may be introduced using any method known in the art. In the microorganism of the present invention, the term "inactivation" is intended to mean that NCgl2053 dehydrogenase gene is expressed lower than the expression of a wild strain or is not expressed at all, or even if the NCgl2053 dehydrogenase gene is expressed into NCgl2053 dehydrogenase, the NCgl2053 dehydrogenase does not have activity at all or have attenuated activity.

In an embodiment of the present invention, the inactivation may be introduced using a method of mutagenesis selected from the group consisting of insertion mutagenesis by insertion of at least one base pair into the NCgl2053 dehydrogenase gene, deletion mutagenesis by deletion of at least one base pair in the NCgl2053 dehydrogenase gene, and transition or transversion mutagenesis by the incorporation of a non-sense codon.

In an embodiment of the present invention, the inactivation may be introduced by transforming a bacterium belonging to the genus *Corynebacterium* with a vector having an antibiotic marker and a partial region of the NCgl2053 dehydrogenase gene and culturing the transformed bacterium under the antibiotics. For example, the vector can be pCR-2053, which includes part of a NCgl2053 gene of SEQ ID No:2. The transformation of a vector having a part of the gene into the microorganism and the culturing under the selected marker lead to homologous recombination of part of a sequence of the gene and an inherent gene of the microorganism. The inherent gene of the microorganism is recombined through the homologous recombination, and of the microorganism having the recombinant gene, only the recombinant microorganism having the above-described marker is selected. As a result, the microorganism that belongs to the genus *Corynebacterium* and has the inactivated inherent NCgl2053 dehydrogenase gene can be obtained. However, a method of obtaining the microorganism of the present invention is not limited to this homologous recombination, and any method known in the art may be used.

The microorganism may be *Corynebacterium glutamicum* KFCC10881-CJP5102 (Accession No. KCCM-10709P).

According to another aspect of the present invention, there is provided a method of producing L-lysine, the method including: culturing the microorganism of the present invention to produce L-lysine in a medium or cells and collecting L-lysine from the culture.

In the method of the present invention, the microorganism of the genus *Corynebacterium* may be cultured using any culture conditions and method known in the art. An example of a culture medium for culturing the *Corynebacterium* strain is the culture medium disclosed in the Manual of Methods for General Bacteriology by the American Society for Bacteriology (Washington D.C., USA, 1981). Carbohydrate sources that can be used in the medium include the following: sugars and carbohydrates such as glucose, saccharose, lactose, fructose, maltose, starch and cellulose; oils and fats such as soybean oil, sunflower oil, castor oil, and coconut oil; fatty acids such as palmitic acid, stearic acid and linolenic acid; alcohols such as ethanol; and organic acids such as acetic acid. The examples of sugar sources mentioned above can be used alone or in combination. Examples of nitrogen sources include the following: peptone, yeast extracts, meat extracts, malt extracts, corn steep liquor, soybean meal, and urea or inorganic compounds such as ammonium sulfate, ammonium chloride, ammonium phosphate, ammonium carbonate, ammonium and nitrate. The above nitrogen sources can be used alone or in combination. Examples of phosphorus sources include the following: potassium dihydrogen phosphate, dipotassium hydrogen phosphate, or corresponding sodium salts thereof. Also, the culture medium can include metal salts, such as magnesium sulfate or iron sulfate, which is necessary for growth. In addition, essential materials for growth such as amino acids and vitamins can be used in addition to the above ingredients. Moreover, proper precursors can be used in the culture medium. The above ingredients can be added to the culture medium during the cultivation in a batchwise or continuous manner.

The pH of the medium can be controlled using a basic compound such as sodium hydroxide, potassium hydroxide or ammonia, or an acid compound such as phosphoric acid or sulphuric acid. Also, the use of an antifoaming agent such as fatty acid polyglycol ester can suppress foam generation. Oxygen or an oxygen-containing gas such as air can be injected into the medium in order to maintain aerobic condition. The temperature of the medium is 20 to 45° C., preferably 25 to 40° C. The culturing can be performed until a desired quantity of L-lysine is produced, but the culturing is desirably performed for 10 to 160 hours.

The culture can be performed in a various manner including batch, fed batch, repeated fed batch and continuous manner. This method is well known in the art, and the present invention is not limited thereto.

L-amino acid can be separated and analysed through anion exchange chromatography and ninhydrin derivative generation.

To develop the microorganism and the method of the present invention, the inventors of the present invention first cultured *Corynebacterium glutamicum* ATCC 13032 in the presence of L-lysine, analysed levels of proteins expressed from the *Corynebacterium glutamicum* ATCC 13032 using two-dimensional electrophoresis, and compared the levels of proteins expressed with those of comparative experiments in which culturing was performed without L-lysine. As a result, we identified proteins which are over-expressed in the presence of L-lysine, that is, proteins presumably to be induced by the presence of lysine. Based on information of the identified proteins, gene information of the above proteins was determined using the US National Institutes of Health GenBank (NIH GenBank), and the proteins were confirmed to be NCgl1835 and NCgl2053.

In addition, it was confirmed whether the above genes are actually induced in the presence of lysine. First, a nucleic acid region considered to be a promoter of the above genes was amplified by PCR, and then the amplified promoter nucleic acid was fused with LacZ gene whose promoter was removed, to obtain a fusion gene of the promoter of the above identified genes-LacZ coding sequence. The obtained fusion gene was inserted into a vector and the vector was introduced into a microorganism. The obtained microorganism was cultured in presence of lysine, and it was confirmed whether the lacZ protein is expressed by measuring the activity of β-galactosidase. As a result, it was confirmed that expression of the above genes is induced by lysine.

However, it is not known how the above genes are associated with the biosynthesis of lysine in the lysine producing microorganism. The inventors of the present invention measured the quantity of produced lysine by inactivating the inherent NCgl2053 gene of a *Corynebacterium* microorganism and confirmed that the quantity of produced lysine was actually increased, in addition to the identification of the genes over-expressed in the presence of lysine.

EXAMPLES

The present invention will now be described in further detail with reference to the following examples. These examples are for illustrative purposes only, and are not intended to limit the scope of the present invention.

In the following examples, a recombinant microorgansim was prepared by inactivating the inherent NCgl2053 gene of *Corynebacterium glutamicum* KFCC10881, the recombinant microorgansim cultured to produce lysine in the culture, and the quantity of produced lysine was measured.

Example 1

Production of Vector to Inactivate Inherent NCgl2053 Gene of Microorganism of the Genus *Corynebacterium*

In this example, in order to produce a vector having an antibiotic marker and part of the DNA sequence of NCgl2053, a gene fragment of NCgl2053 of about 500 bp (SEQ. ID. NO. 2; 170 to 650 nucleotides of SEQ. ID. No 1) was amplified using a PCR using the oligonucleotides of SEQ ID. NOS. 3 and 4 as primers and the chromosome DNA of *Corynebacterium glutamicum* ATCC 13032 as a template. The PCR was repeated 30 times by denaturing at a temperature of 96° C. for 30 seconds, annealing at a temperature of 52° C. for 30 seconds, and polymerizing at a temperature of 72° C. for 30 seconds. The amplified NCgl2053 gene fragment was inserted into *E. coli* plasmid pCF2.1 by using a TOPO Cloning Kit (Invitrogen, US) to produce a pCR-2053 plasmid. FIG. 1 shows a pCR-2053 vector in which a NCgl2053 gene fragment of about 500 bp was cloned.

Example 2

Production of L-Lysine Producing Strain Having Inactivated Inherent NCgl2053 gene of *Corynebacterium glutamicum* KFCC10881

Using the transformation method illustrated in Appl. Microbiol. Biotechnol. (1999) 52:541-545, *Corynebacterium glutamicum* KFCC10881, which is an L-lysine producing stain, was transformed with the pCR-2053 plasmid produced in Example 1 by an electric pulse method, and then the transformed microorganism was cultured the selection medium containing 25 mg/L of kanamycin. A PCR was performed using the chromosomal DNA of the transformed strains as a template on the second day of culturing in order to confirm whether NCgl2053 genes were destroyed. The PCR was performed by using the oligonucleotides of SEQ ID. NO. 5 and 6 as primers and the chromosomal DNA of the transformed strains as template to amplify a gene fragment of NCgl2053 with a length of about 5150 bp (118 to 775 nucleotides of SEQ ID. NO. 1) containing pCR-2053 plasmid. As a result, a *Corynebacterium glutamicum* KFCC10881 strain that the above genes were destroyed, was obtained, and then named as *Corynebacterium glutamicum* KFCC10881-CJP5102. It is considered that the above genes are destroyed by incorporating the pCR-2053 plasmid into the middle of inherent NCgl2053 genes of a chromosomal DNA through the homologous recombination.

The *Corynebacterium glutamicum* KFCC10881-CJP5102 strain was deposited on November 16, 2005 at the Korean Culture Center of Microorganisms, 361-221, Yurim B/D, Hongie-1-dong, Seodaemun-gu, Seoul 120-091, Republic of Korea, which is an International Depository Authority (IDA) under the Budapest Treaty (Accession No. KCCM-10709P).

Example 3

Production of L-lysine using *Corynebacterium glutamicum* KFCC10881-CJP5102

L-lysine was produced by culturing the *Corynebacterium glutamicum* KFCC10881-CJP5102 strain produced in Example 2.

First, a 250 ml corner-baffled flask having 25 ml of the seed medium described below was inoculated with *Corynebacterium glutamicum* parent strain KFCC10881, and KFCC10881-CJP5102, and the resultant was cultured while stirring at 200 rpm at 30° C. for 20 hours. 1 mL of the resulting culture solution was inoculated to a 250 ml corner-baffled flask containing 24 ml of the production medium described below, and the result was cultured while stirring at 200 rpm at 30° C. for 120 hours. After the culturing was finished, the quantity of produced L-lysine was measured using an HPLC (Waters 2457.) As a result, it was determined that *Corynebacterium glutamicum* KFCC10881 and KFCC10881-CJP5102 respectively produced 45 g/l and 49 g/l of L-lysine in a hydrochloride form in the culture.

| Seed culture medium (pH 7.0) (per liter of distilled water) | |
|---|---|
| raw sugar | 20 g |
| peptone | 10 g |
| yeast extract | 5 g |
| urea | 1.5 g |
| $KH_2PO_4$ | 4 g |
| $K_2HPO_4$ | 8 g |
| $MgSO_4 7H_2O$ | 0.5 g |
| biotin | 100 μg |
| thiamine HCl | 1000 μg |
| calcium-pantothenic acid | 2000 μg |
| nicotinamide | 2000 μg |

| Production medium (pH 7.0) (per liter of distilled water) | |
|---|---|
| raw sugar | 100 g |
| $(NH_4)_2SO_4$ | 40 g |
| soybean protein | 2.5 g |
| corn steep solids | 5 g |
| urea | 3 g |
| $KH_2PO_4$ | 1 g |
| $MgSO_4 7H_2O$ | 0.5 g |
| biotin | 100 μg |
| thiamine hydrochloride | 1000 μg |
| calcium-pantothenic acid | 2000 μg |
| nicotinamide | 3000 μg |
| $CaCO_3$ | 30 g |

Example 4

Collection of L-lysine from Culture Medium of *Corynebacterium glutamicum* KFCC10881-CJP5102 Strain By adding hydrochloride to 1 L of a lysine fermentation broth obtained by culturing *Corynebacterium glutamicum* KFCC10881-CJP5102 in a medium containing molasses and raw sugar, the pH of the fermentation broth was adjusted to pH 2.0, and Ca ions were transformed into $CaSO_4$ and $CaCl_2$. Then, the culture materials flowed into a cation exchange resin (Diaion SK-L10) reproduced in the form of ammonium ions in the upward direction, and adhering the lysine to the resin. After residual bacteria within the cation exchange resin were removed by washing with demineralized water, the high-concentrated lysine was collected by eluting the resin with 2N-ammonium hydroxide. The collected solution was concentrated and crystallized by cooling to 20° C., while adjusting the pH at 5.0. A first wet product was obtained by centrifugal separation of a crystallization-completed slurry and a second wet product was obtained by batch concentrating and crystallizing the mother solution. 46.5 g of a dried lysine product with 98.5% lysine content was obtained by combining the first and second wet products and drying the combined product.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An isolated *Corynebacterium glutamicum*, which has an inactivated inherent NCgl2053 dehydrogenase gene having a nucleotide sequence as set forth in SEQ. ID NO: 1 and which produces L-lysine.

2. The isolated *Corynebacterium glutamicum* of claim 1, which is obtained by a method of mutagenesis selected from the group consisting of insertion mutagenesis by insertion of at least one base pair into an NCgl2053 dehydrogenase gene having a nucleotide sequence as set forth in SEQ ID NO: 1, deletion mutagenesis by deletion of at least one base pair in an NCgl2053 dehydrogenase gene having a nucleotide sequence as set forth in SEQ ID NO: 1, and transition or transversion mutagenesis by incorporation of a non-sense codon.

3. The isolated *Corynebacterium glutamicum* of claim 1, which is selected by transforming vectors having an antibiotic marker with part of the NCgl2053 dehydrogenase gene having a nucleotide sequence as set forth in SEQ ID NO: 1 and cultured under the antibiotic.

4. The isolated *Corynebacterium glutamicum* of claim 1, which is *Corynebacterium glutamicum* KFCC10881-CJP5102 (Deposition No. KCCM-10709P).

5. A method of producing L-lysine comprising:
   culturing the isolated *Corynebacterium glutamicum* according to claim 1 to produce L-lysine in cultures or cells; and
   collecting L-lysine from the cultures.

6. A method of producing L-lysine comprising:
   culturing the isolated *Corynebacterium glutamicum* according to claim 2 to produce L-lysine in cultures or cells; and
   collecting L-lysine from the cultures.

7. A method of producing L-lysine comprising:

culturing the isolated *Corynebacterium glutamicum* according to claim 3 to produce L-lysine in cultures or cells; and collecting L-lysine from the cultures.

8. A method of producing L-lysine comprising:

culturing the isolated *Corynebacterium glutamicum* according to claim 4 to produce L-lysine in cultures or cells; and collecting L-lysine from the cultures.

* * * * *